(12) United States Patent
Wang

(10) Patent No.: US 10,945,916 B2
(45) Date of Patent: Mar. 16, 2021

(54) FOOT SPA

(71) Applicant: Mei-Yun Wang, Taipei (TW)

(72) Inventor: Mei-Yun Wang, Taipei (TW)

( * ) Notice: Subject to any disclaimer, the term of this patent is extended or adjusted under 35 U.S.C. 154(b) by 179 days.

(21) Appl. No.: 16/174,265

(22) Filed: Oct. 29, 2018

(65) Prior Publication Data

US 2019/0240111 A1 Aug. 8, 2019

(30) Foreign Application Priority Data

Feb. 2, 2018 (TW) .................................. 107201688

(51) Int. Cl.
*A61H 35/00* (2006.01)
*A61N 1/44* (2006.01)
*A61H 33/00* (2006.01)

(52) U.S. Cl.
CPC ....... *A61H 35/006* (2013.01); *A61H 33/6047* (2013.01); *A61H 33/6052* (2013.01); *A61H 33/6073* (2013.01); *A61N 1/445* (2013.01); *A61H 2033/0037* (2013.01)

(58) Field of Classification Search
CPC .... C25B 1/04; C25B 9/06; C25B 9/00; C25B 11/12; C25B 9/12; C25B 9/18; C25B 9/206
See application file for complete search history.

(56) References Cited

U.S. PATENT DOCUMENTS

2011/0253639 A1* 10/2011 Kook .................... C02F 1/4674
210/746

\* cited by examiner

*Primary Examiner* — Zulmariam Mendez
(74) *Attorney, Agent, or Firm* — Hershkovitz & Associates, PLLC; Abe Hershkovitz

(57) ABSTRACT

A foot spa includes a body and an electrolysis device. The body has a receiving space for containing water. The electrolysis device is mounted on a bottom of the body and includes a case, a control module and two electrolyte plates. The control module is mounted inside the body. The two electrolyte plates are mounted on a top portion of the case and are electrically connected to the control module. When the foot spa is operated, salt water is added to the receiving space for the two electrolyte plates to be soaked into the salt water in generation of an electrolytic reaction, such that sodium hydroxide and hypochlorous acid can be generated from the salt water to sterilize and deodorize the feet of users and provide the hygienic advantage.

16 Claims, 4 Drawing Sheets

FOOT SPA

BACKGROUND OF THE INVENTION

1. Field of the Invention

The present invention relates to a foot spa and, more particularly, to a foot spa with enhanced sterilizing and deodorant effect.

2. Description of the Related Art

Because of long sitting period in the office or standing too much at work, feet of modern people may be the portions of the body that are subject to a overloaded and exhausted condition and poor blood circulation, and toxin accumulated in the feet out of the metabolism process also causes the feet to swell and feel stiff, heavy or painful.

With reference to FIG. 4, a conventional foot spa includes a body 81, an opening 81 formed at a top portion of the body 10, and a receiving space 83 defined inside the body 10 to communicate with the opening 81. The receiving space 83 serves to contain hot water for users to put their feet in the receiving space 83. Blood circulation of the feet can thus be simulated first by the hot water temperature and then takes effect to promote blood circulation of the entire body, such that users can relieve stiffness of muscles of the feet. Meanwhile, hot water makes users sweat to attain the effect of expelling toxins.

Although toxins can be removed by submerging the feet in hot water, the expelled toxins may be dissolved into the hot water and again be attached to the skin of the feet. It may result in skin allergies, skin inflammation, or unpleasant odor. Despite salt added to hot water somehow having the disinfection effect, the disinfection effect is limited and the added salt appears to be an unsatisfactory solution for sterilization and deodorant effect.

SUMMARY OF THE INVENTION

An objective of the present invention is to provide a foot spa with an electrolysis device installed therein to electrolyze salt water in the foot spa so as to generate chemical compounds for the purpose of sterilization and deodorization.

To achieve the foregoing objective, the foot spa includes a body and an electrolysis device.

The body has a receiving space and an opening.

The receiving space is defined in the body.

The opening is formed at a top portion of the body and communicates with the receiving space.

The electrolysis device is mounted on a bottom portion of the body and has a case, a control module, a first electrolyte plate and a second electrolyte plate.

The control module is mounted inside the case.

The first electrolyte plate and the second electrolyte plate are electrically connected to the control module and are mounted on a top portion of the case.

Given the foregoing structure, when the foot spa is in use with the receiving space of the body filled with salt water, an electrolytic reaction occurs when the first electrolyte plate and the second electrolyte plate of the electrolysis device are submerged in the salt water and chemical compounds with sterilizing and deodorant effect, such as sodium hydroxide and hypochlorous acid, can be generated from the electrolysis to sterilize and deodorize users' feet in an enhanced hygienic fashion.

Other objectives, advantages and novel features of the invention will become more apparent from the following detailed description when taken in conjunction with the accompanying drawings.

DETAILED DESCRIPTION OF THE INVENTION

Figure 1:
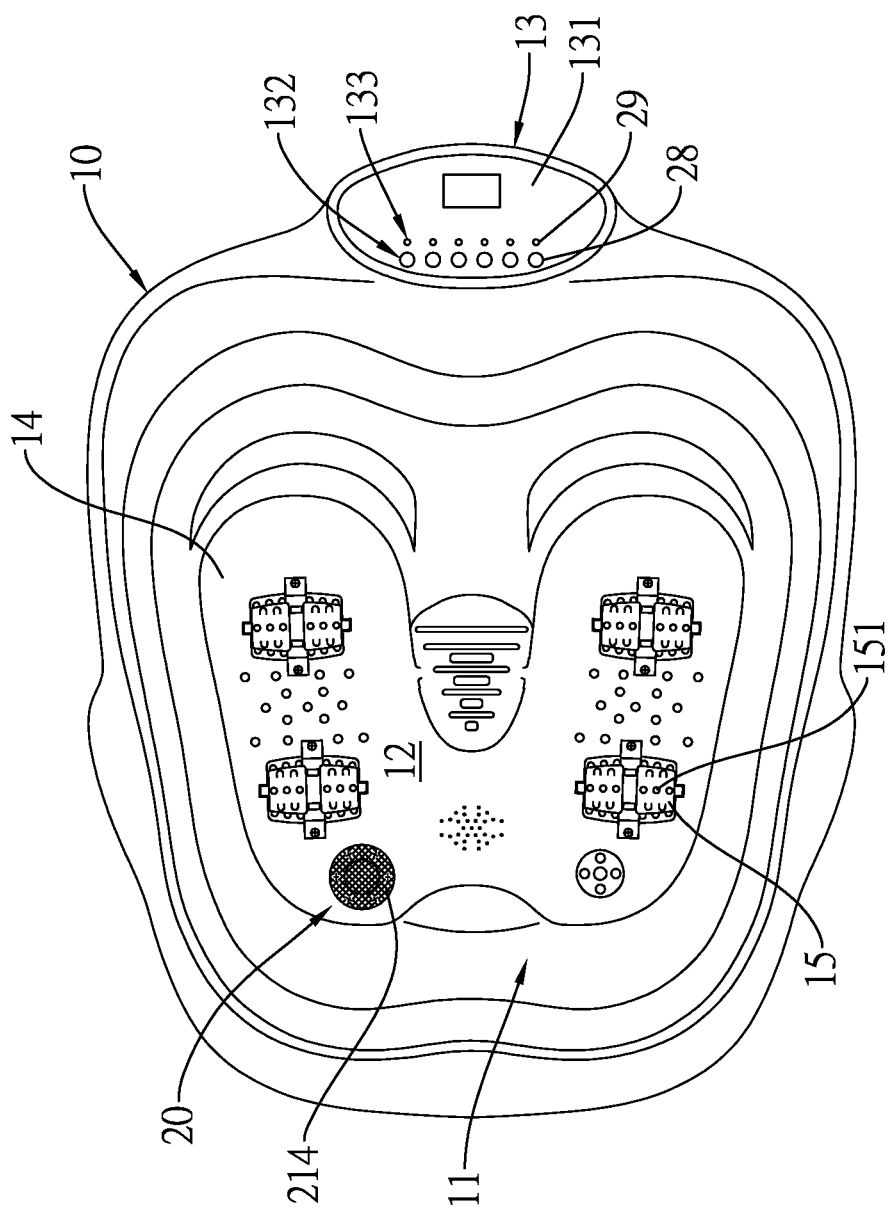
FIG. 1 is a top view of a foot spa in accordance with the present invention.
Figure 2:
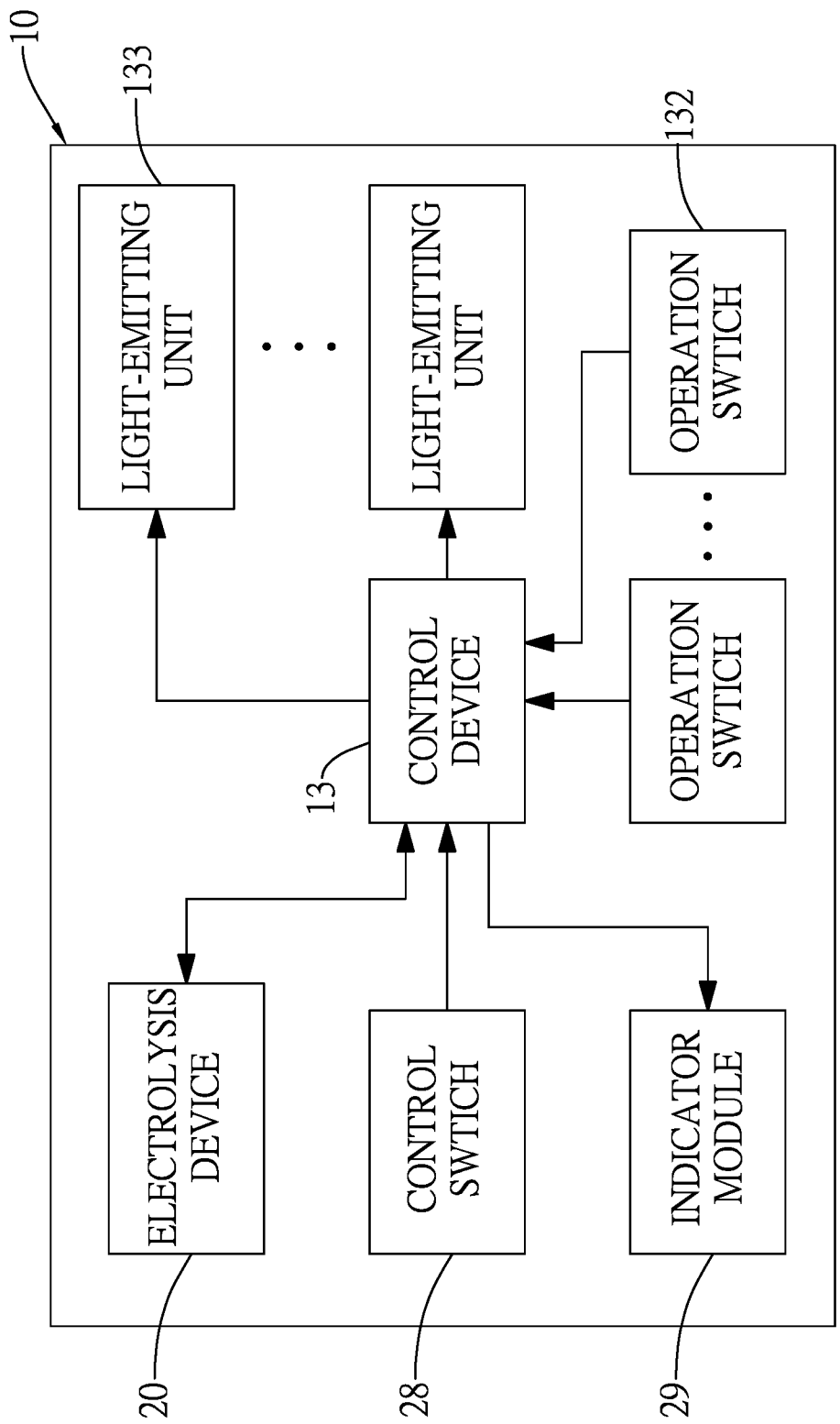
FIG. 2 is a functional diagram of circuit architecture of the foot spa in FIG. 1.

With reference to FIGS. 1 and 2, a foot spa in accordance with the present invention includes a body 10 and an electrolysis device 20. The electrolysis device 20 is mounted on a bottom portion of the body 10 and is electrically connected to a circuit loop of the body 10.

The body 10 takes the form of a washbowl and has an opening 11 formed at a top portion of the body 10. The body 10 has a receiving space 12 defined therein for the electrolysis device 20 to be received in a top portion of the receiving space 12 and communicating with the opening 11. The receiving space 12 serves to contain water and salt that are mixed into salt water. Depending on users' preference, hot water or cold water can be selected to mix the salt water. In the present embodiment, the body 10 includes a control device 13 mounted on a top edge portion of the body 10. The electrolysis device 20 is electrically connected to the control device 13. The control device 13 includes a control panel 131 with multiple operation switches 132 and multiple light-emitting units 133 mounted on the control panel 131. The multiple operation switches 132 and the light-emitting units 133 are electrically connected to the control device 13. Each operation switch 132 and a light-emitting unit 133 corresponding to the operation switch 132 turn on/off one of multiple functions of the foot spa but are not limited to correspondence of the function. When receiving a signal triggered by touching one of the multiple operation switches 132, the control device 13 controls a corresponding function of the foot spa and transmits a driving signal to a corresponding light-emitting unit 133 for the corresponding light-emitting unit 133 to be lit or unlit. Specifically, when the light-emitting unit 133 is lit, it represents that the function of the foot spa associated with the corresponding operation switch 132 is activated. When the light-emitting unit 133 is unlit, it represents that the function of the foot spa associated with the corresponding operation switch 132 is deactivated. The lit/unlit description is provided for exemplification but not limitation.

The body 10 has two foot rests 14 parallelly formed in the bottom portion of the body 10 and adjacent to a bottom portion of the receiving space 12 for users to rest their feet on the respective foot rests 14. The two foot rests 14 may or may not communicate with each other.

Each foot rest 14 has at least one roller 15 mounted thereon and each roller 15 has multiple nubs 151 formed on and protruding outwards from a periphery of the roller 15. Users can step their feet on the nubs 151 to massage acupoints on the footpads. In the present embodiment, each foot rest 14 has two rollers 15 parallelly mounted thereon, such that a front portion and a rear portion of the footpad can be simultaneously massaged.

Figure 3:
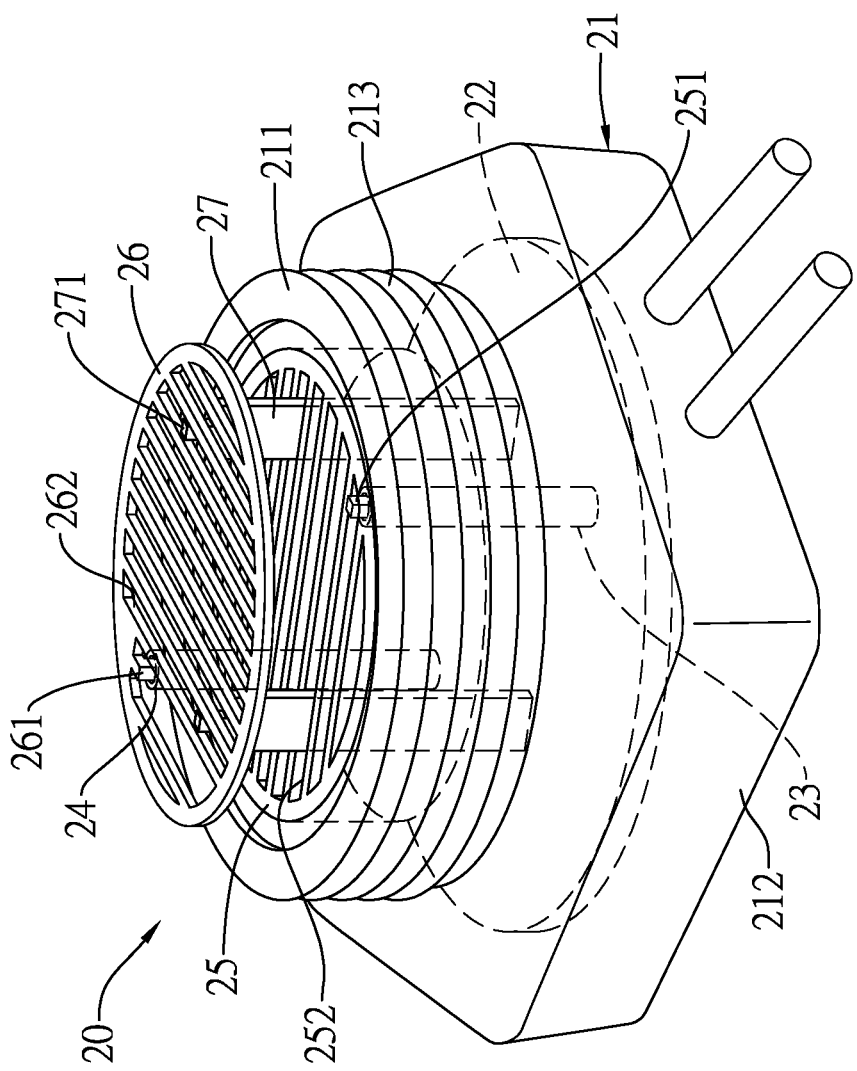
FIG. 3 is a perspective view of an electrolysis device of the foot spa in FIG. 1.
Figure 4:
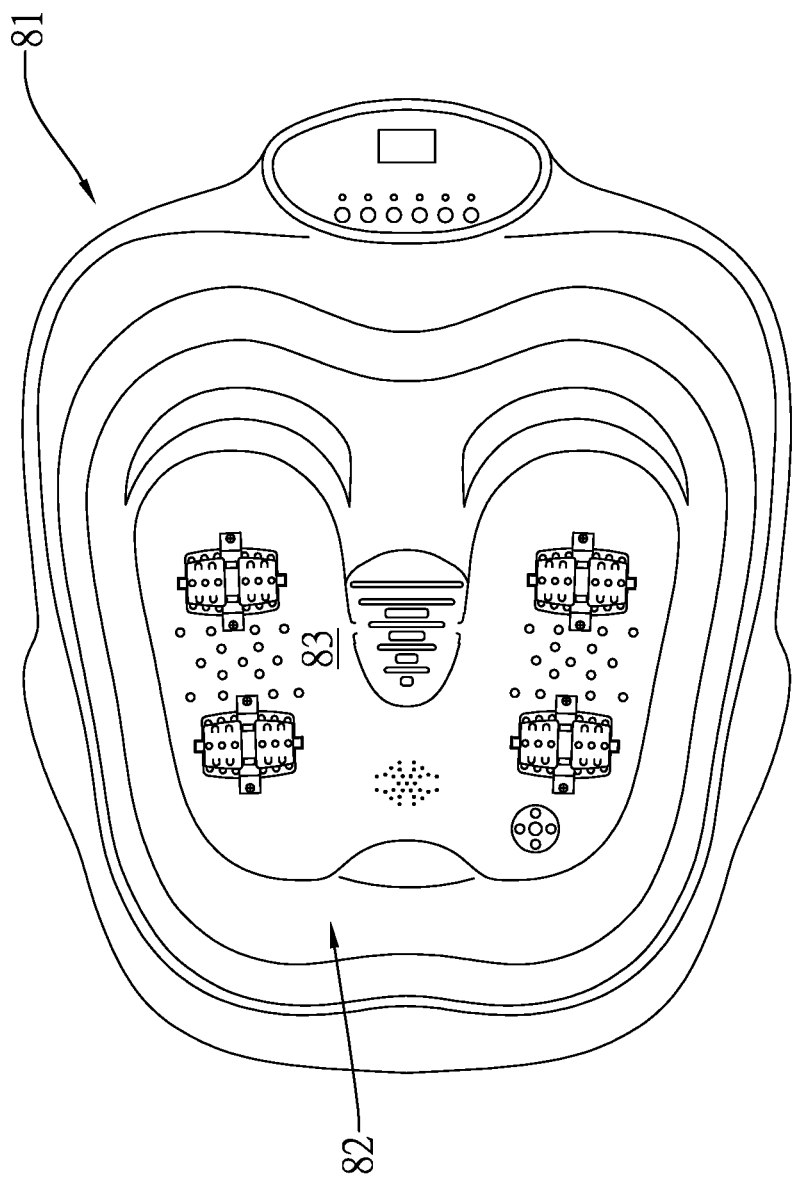
FIG. 4 is a top view of a conventional foot spa.

With reference to FIG. 3, to depict detailed structure of the electrolysis device 20, the electrolysis device 20 includes a case 21, a control module 22, a first tube 23, a second tube 24, a first electrolyte plate 25, and a second electrolyte plate 26. The control module 22, the first tube 23 and the second tube 24 are mounted inside the case 21. The first electrolyte plate 25 and the second electrolyte plate 26 are mounted on a top portion of the case 21. In the present embodiment, the first electrolyte plate 25 and the second electrolyte plate 26 are parallel to each other, and the control module 22 is a circuit board.

The case 21 has a top housing 211 and a bottom housing 212. A bottom surface of the top housing 211 is formed on a top surface of the bottom housing 212. The bottom housing 212 has an internal space for the control module 22 to be installed in the internal space. The control module 22 is connected to the power loop of the body 10 and is electrically connected to the control device 13 of the body 10. A lower end of the first tube 23 penetrates into the internal space of the bottom housing 212 through the top housing 211 and an upper end of the first tube 23 is flush with a top surface of the top housing 211 for a portion of the top surface of the top housing 211 formed through by the first tube 23 to communicate with the internal space of the bottom housing 212 through the first tube 23. A lower end of the second tube 24 penetrates into the internal space of the bottom housing 212 and an upper end of the second tube 24 is exposed beyond the top surface of the top housing 211 for an external space outside the case 21 to communicate with the top surface of the top housing 211 formed through by the second tube 24 and the internal space of the bottom housing 212 through the second tube 24. In the present embodiment, the top housing 211 and the bottom housing 212 are integrally formed, and the top housing 211 is smaller than the bottom housing 212 in outer diameter to constitute a stepwise structure.

The top housing 211 has a coupling portion 213 formed on a peripheral surface thereof for the electrolysis device 20 to be mounted on the bottom portion of the body 10 of the foot spa. Preferably, the coupling portion 213 is a threaded portion. With reference to FIG. 1, when the electrolysis device 20 is mounted inside the body 10 of the foot spa, the electrolysis device 20 further has a protection cover 214 mounted on a top thereof to protect the electrolysis device 20.

With further reference to FIG. 3, the first electrolyte plate 25 is circular and grid-shaped, and is horizontally placed on the top surface of the top housing 211. A first conducting strip 251 is mounted through the first electrolyte plate 25 and the first tube 23 with one end thereof electrically connected to the first electrolyte plate 25 and the other end thereof electrically connected to the control module 22. The second electrolyte plate 26 is circular and grid-shaped, is horizontally placed on the upper end of the second tube 24, and is parallel to the first electrolyte plate 25. A second conducting strip 261 is mounted through the second electrolyte plate 26 and the second tube 24 with one end thereof electrically connected to the second electrolyte plate 26 and the other end thereof electrically connected to the control module 22. In the present embodiment, the first electrolyte plate 25 and the second electrolyte plate 26 are made from a titanium-platinum alloy, an iridium titanium oxide material, a graphite material, or a pure platinum material.

In the present embodiment, the first electrolyte plate 25 has multiple first slots 252 formed through the first electrolyte plate 25, such that the salt water contained in the receiving space 12 can be in full contact with an external surface of the first electrolyte plate 25.

In the present embodiment, the second electrolyte plate 26 has multiple second slots 262 formed through the second electrolyte plate 26, such that the salt water contained in the receiving space 12 can be in full contact with an external surface of the second electrolyte plate 26.

The electrolysis device 20 further includes at least one support bar 27. Each of the at least one support bar 27 sequentially penetrates through the first electrolyte plate 25 and the top housing 211 with a lower end of the support bar 27 mounted on the top surface of the bottom housing 212 and an upper end of the support bar 27 mounted through one of the multiple first slots 252 and abutting against a bottom surface of the second electrolyte plate 26 so as to better support the second electrolyte plate 26. Each of the at least one support bar 27 has a reduced boss 271 formed on and protruding upwards from the upper end of the support bar 27. The reduced boss 271 is mounted in one of the multiple second slots 262 to position the second electrolyte plate 26. In the present embodiment, there are two support bars 27 that are parallel to each other for the purpose of better positioning the second electrolyte plate 26.

In the present embodiment, protection adhesive is filled between the top housing 211 and the bottom housing 212 to raise the waterproof effect of the electrolysis device 20 and protect the control module 22. Protection adhesive is also filled in the first tube 23 and the second tube 24 to increase the waterproof effect of the electrolysis device 20 and protect the control module 22.

The electrolysis device 20 further has a control switch 28 mounted on the control panel 131 as shown in FIG. 1 and electrically connected to the control device 13 as shown in FIG. 2. When users press the control switch 28, a control signal is transmitted to the control device 13 and the control device 13 further transmits the control signal to the control module 22 of the electrolysis device 20 for the control module 22 to turn on or turn off the electrolysis device 20.

The electrolysis device 20 further has an indicator module 29 mounted on the control panel 131 as shown in FIG. 1 and electrically connected to the control device 13 as shown in FIG. 2. The indicator module 29 indicates a state of the concentration of the salt water contained in the receiving space 12 and detailed operation associated therewith is described as follows.

When the foot spa is operated and after users pour water into the receiving space 12 of the body 10 through the opening 11, salt is added to the water for the control module 22, the first electrolyte plate 25, the salt water, and the second electrolyte plate 26 to form a loop. After the control module 22 constantly or intermittently outputs a current signal to the second electrolyte plate 26 and the current signal further sequentially passes through the salt water and the first electrolyte plate 25 in generation of an electrolytic reaction, the control module 22 receives a returned current signal from the second electrolyte plate 26. When the control module 22 determines that the returned current signal is greater than a preset value, it indicates that the concentration of the salt water is normal. Then, the control module 22 transmits a signal to the control device 13 and the control device 13 sends a driving signal to the indicator module 29 according to the signal for the indicator module 29 to emit light with a first color indicative of a normal concentration of the salt water.

When users add salt that is more than enough, the control module 22 determines that the returned current signal is smaller than the preset value, indicating that the concentration of the salt water is abnormal. Then, the control module 22 transmits a signal to the control device 13 and the control device 13 sends a driving signal to the indicator module 29 according to the signal for the indicator module 29 to emit light with a second color indicative of an abnormal concentration of the salt water.

The light with the first color and the light with the second color may be blue light and red light respectively but are not limited thereto.

By virtue of electrolytic reaction between the electrolysis device 20 and the salt water, the salt water can be electrolyzed to generate chemical compounds, such as sodium hydroxide and hypochlorous acid, to provide a sterilizing and deodorant effect.

In sum, the present invention has the following advantages:

1. The concentration of the salt water can be determined by the electrolysis device and is signaled by the indicator module 29 for users to be aware if the concentration of the salt water is normal.

2. The salt water is electrolyzed by the electrolysis device 20 to generate sodium hydroxide and hypochlorous acid to provide a sterilizing and deodorant effect.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A foot spa comprising:
   a body having:
      a receiving space defined therein; and
      an opening formed at a top portion of the body and communicating with the receiving space;
   an electrolysis device mounted on a bottom portion of the body and having:
      a case;
      a control module mounted inside the case; and
      a first electrolyte plate and a second electrolyte plate electrically connected to the control module and mounted on a top portion of the case;
   wherein the electrolysis device further includes a first tube and a second tube mounted inside the case, wherein the first electrolyte plate is mounted on an upper end of the first tube, a first conducting strip is mounted through the first tube to electrically connect the first electrolyte plate to the control module, an upper end of the second tube is exposed beyond a top surface of the case, the second electrolyte plate is placed on the upper end of the second tube, and a second conducting strip is mounted through the second tube to electrically connect to the control module.

2. The foot spa as claimed in claim 1, wherein the first electrolyte plate has multiple first slots formed through the first electrolyte plate, and the second electrolyte plate has multiple second slots formed through the second electrolyte plate.

3. The foot spa as claimed in claim 2, wherein the case of the electrolysis device includes at least one support bar, and each of the at least one support bar is mounted through one of the multiple first slots to abut against a bottom surface of the second electrolyte plate.

4. The foot spa as claimed in claim 3, wherein each of the at least one support bar has a reduced boss formed on and protruding upwards from an upper end of the support bar and mounted in one of the multiple second slots of the second electrolyte plate.

5. The foot spa as claimed in claim 4, wherein the body further includes a control device mounted on a top edge portion of the body, and the control device has a control panel and is electrically connected to the control module of the electrolysis device.

6. The foot spa as claimed in claim 1, wherein the control module of the electrolysis device transmits a current signal to the second electrolyte plate and the current signal sequentially passes through salt water filled in the receiving space of the body and the first electrolyte plate to generate an electrolytic reaction.

7. The foot spa as claimed in claim 5, wherein the electrolysis device further includes a control switch mounted on the control panel for users to turn on or turn off the electrolysis device.

8. The foot spa as claimed in claim 5, wherein the electrolysis device further includes an indicator module mounted on the control panel and electrically connected to the control device, the control module of the electrolysis device receives a returned current signal from the second electrolyte plate and transmits a signal to the control device for the control device to send a driving signal to the indicator module to drive the indicator module to emit light.

9. The foot spa as claimed in claim 1, wherein the first electrolyte plate and the second electrolyte plate are made from a titanium-platinum alloy, an iridium titanium oxide material, a graphite material, or a pure platinum material.

10. The foot spa as claimed in claim 2, wherein the first electrolyte plate and the second electrolyte plate are made from a titanium-platinum alloy, an iridium titanium oxide material, a graphite material, or a pure platinum material.

11. The foot spa as claimed in claim 3, wherein the first electrolyte plate and the second electrolyte plate are made from a titanium-platinum alloy, an iridium titanium oxide material, a graphite material, or a pure platinum material.

12. The foot spa as claimed in claim 4, wherein the first electrolyte plate and the second electrolyte plate are made from a titanium-platinum alloy, an iridium titanium oxide material, a graphite material, or a pure platinum material.

13. The foot spa as claimed in claim 5, wherein the first electrolyte plate and the second electrolyte plate are made from a titanium-platinum alloy, an iridium titanium oxide material, a graphite material, or a pure platinum material.

14. The foot spa as claimed in claim 6, wherein the first electrolyte plate and the second electrolyte plate are made from a titanium-platinum alloy, an iridium titanium oxide material, a graphite material, or a pure platinum material.

15. The foot spa as claimed in claim 7, wherein the first electrolyte plate and the second electrolyte plate are made from a titanium-platinum alloy, an iridium titanium oxide material, a graphite material, or a pure platinum material.

16. The foot spa as claimed in claim 8, wherein the first electrolyte plate and the second electrolyte plate are made from a titanium-platinum alloy, an iridium titanium oxide material, a graphite material, or a pure platinum material.

* * * * *